United States Patent [19]
Sprinkle et al.

[11] Patent Number: 5,374,400
[45] Date of Patent: Dec. 20, 1994

[54] TWO-STAGE GAS MEASUREMENT SYSTEM

[75] Inventors: Danny R. Sprinkle, Newport News; Tony T. D. Chen, Norfolk; Sushil K. Chaturvedi, Virginia Beach, all of Va.

[73] Assignee: The United States of America as represented by the Administrator of the National Aeronautics and Space Administration, Washington, D.C.

[21] Appl. No.: 879,480

[22] Filed: May 7, 1992

[51] Int. Cl.$^5$ ............................................. G01N 27/12
[52] U.S. Cl. ........................................ 422/94; 204/426; 422/88; 422/98
[58] Field of Search ................ 422/88, 90, 94, 95, 422/98; 204/410, 424, 426, 427

[56] References Cited

U.S. PATENT DOCUMENTS

| | | | |
|---|---|---|---|
| 4,341,108 | 7/1982 | Warncke et al. | 422/54 X |
| 4,911,890 | 3/1990 | Singh et al. | 422/98 X |

*Primary Examiner*—Jill A. Johnston
*Attorney, Agent, or Firm*—George F. Helfrich

[57] ABSTRACT

A quick-response, real-time gaseous measurement system allows for the continuous sampling of a low pressure gaseous environment. A sample of test gas from the low pressure gaseous environment is continuously extracted and pumped to a structural tee joint which is open to the atmosphere at one end to maintain the test gas at a constant pressure. The structural tee joint communicates at the other end with a heater for maintaining the test gas at a constant temperature. From the heater, the test gas is sent to a sensor which develops a voltage that is proportional to the partial pressure of the gaseous component to be measured in the test gas, a constant flow rate to test gas being provided through the heater and sensor. Since test gas pressure, temperature, and flow rate are being held constant, changes in sensor voltage are attributable only to changes in the concentration of the measured gas component.

1 Claim, 1 Drawing Sheet

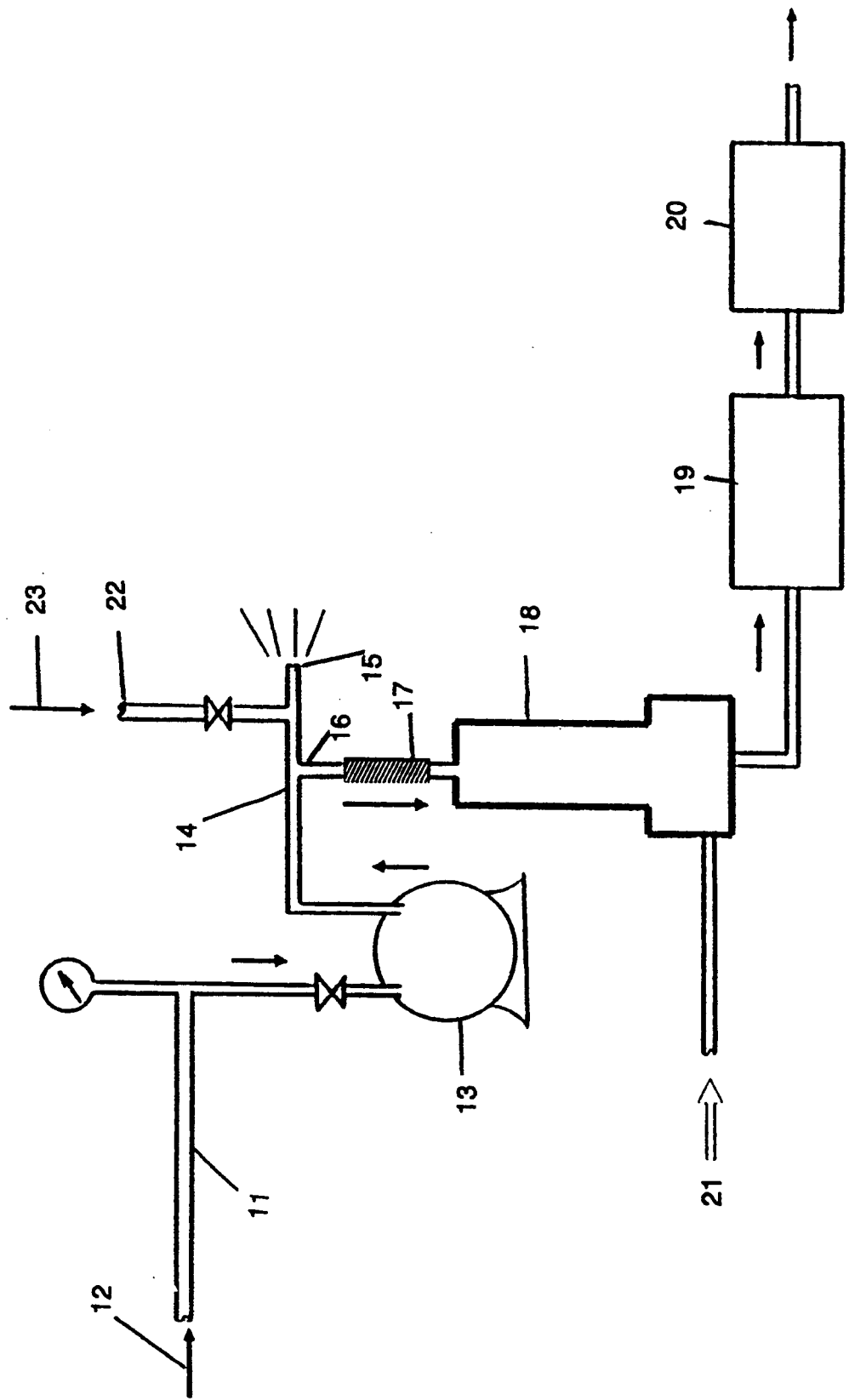

TWO-STAGE GAS MEASUREMENT SYSTEM

ORIGIN OF THE INVENTION

The invention described herein was made jointly by an employee of the United States Government and contract employees under a NASA Contract. In accordance with 35 U.S.C. 202, the contractor elected not to retain title.

BACKGROUND OF THE INVENTION

1. Field of the Invention

The present invention relates generally to gaseous measurement systems. In particular, it relates to a system which provides a quickly responding real-time measurement of test section gaseous, e.g., oxygen, concentration.

2. Description of Related Art

There has been a longstanding need to sample from a gaseous Test environment of fluctuating low pressure, and to continuously monitor the same for gaseous content, e.g., oxygen content. Previous methods have employee both in-situ and sampling techniques for the monitoring of steady, near-atmospheric test environments.

SUMMARY OF THE INVENTION

Accordingly, it is a primary object of the present invention to provide what has not been available in the art, viz., a quickly responding real-time measurement system for sampling a gaseous test environment of fluctuating low pressure. It is another object of the present invention to provide a system for sampling a gaseous test environment of fluctuating low pressure and continuously monitoring the same in real time for gaseous, e.g., oxygen content using a sensor which is sensitive to, and thus must be kept isolated from, pressure and temperature effects of the test environment.

These and other objects and related benefits are obtained by providing a two-stage system wherein a sample of test gas is first pumped from a low pressure test environment and directed to a tee. The tee is open to the atmosphere at one end and communicates with the second stage of the process at the other end. A constant flow rate of test gas is pulled through the second stage by a sample pump and flow controller. A heater tube heats the test gas to a constant temperature, and the open ended tee ensures a constant pressure in the second stage, wherein a sensor is present which develops a voltage proportional to the partial pressure of the component to be measured in the test gas. Reference air, if required by the sensor for optimum operation, is sent to the sensor through a flow controller. A calibration port located near the inlet to the second stage allows gases of various component concentrations to be sent to the sensor for calibration purposes.

BRIEF DESCRIPTION OF THE DRAWING

For a more complete understanding of the present invention, including its primary objects and attending benefits, reference should be made to the Description of the Preferred Embodiments, which is set forth in detail below. This description should be read together with the accompanying drawing, The sole FIGURE of which is a schematic showing the cooperative elements which make up the two-stage gas measurement system according to the present invention.

DESCRIPTION OF THE PREFERRED EMBODIMENTS

Referring now to the drawing, there is shown a sampling tube 11, which is used to continuously remove a sample of test gas 12 from a low pressure test environment (not shown), typically at a pressure of 2 psi.

As an example of a low pressure test environment, the NASA Langley 8-Foot High-Temperature Tunnel is currently being modified to facilitate the testing of air-breathing hypersonic propulsion systems. The working medium of this tunnel is the product of the combustion of methane and air, and, as such, is deficient in the proper amount of oxygen necessary for sustaining test engine operation. This requires the injection of oxygen to the combustor air before combustion to compensate for this post-combustion oxygen deficiency. It is therefore necessary to have a quickly responding real-time measurement of test section oxygen concentration to ensure a proper test environment.

In the first stage of the instant system, extraction pump 13 (for example, a carbon-vane extraction pump, well-known in the art) pumps test gas 12 from the low pressure test environment (not shown) to structural tee joint 14, which is open to the atmosphere (14 psi) at one end 15. The other end 16 of structural tee joint 14 communicates with the second stage of the instant system, which contains the sensor 18. In the NASA Langley 8-Foot High-Temperature Tunnel, where real-time measurement of test section oxygen concentration is necessary to ensure a proper test environment, the sensor 18 is a zirconium oxide-based oxygen sensor, which develops a voltage proportional to the oxygen partial pressure of the test gas. As is understood by those of skill in the art, other components of a test gas could be monitored, employing other such sensors. Accordingly the basic two-sage design of the present measurement system can be utilized to fabricate many gas analysis instruments which must be isolated from pressure and temperature effects of the test environment.

A preferred oxygen sensor 18 is commercially available and is based on a yttrium-stabilized zirconium oxide disc coated with porous platinum. When heated to its operating temperature (1200°–1600° F.), this sensor produces a voltage proportional to the ratio of the partial pressure of oxygen on each side of the disc, according to the following equation:

$$E = AT[ln(P_1/P_2)] = C,$$

where:

E = voltage across the sensor disc
A = arithmetic constant
T = absolute temperature of sensor disc
$P_1$ = partial pressure of $O_2$ in test sample
$P_2$ = partial pressure of $O_2$ in reference air
C = sensor constant.

Before impinging upon sensor 18, the test gas passes through heater tube 17, which heats the sample to the desired constant temperature, while open end 15 of structural tee joint 14 ensures a constant pressure in the second or sensor stage of the present system. Sample pump 20 and flow controller 19 cooperate to pull the sample of test gas through the second stage of the system at a constant flow rate (typically 4 lpm). Reference air 21. which is required by the oxygen sensor specified hereinabove for optimum operation, is sent to the sensor by flow controller 19. Calibration port 22, located near the inlet to the second stage on structural tee joint 14, allows gases of various component (e.g., oxygen) concentrations to be sent to sensor 18 for calibration purposes. Since test gas sample pressure, flow rate, and temperature inside the housing of sensor 18 are being held constant, changes in sensor voltage are attributable only to changes in the concentration of the measured gaseous component (e.g., oxygen).

Several oxygen sensors as specified above were tested for both accuracy and response time. The same set-up, used for both tests is shown in the drawing. The pump 20 and flow controller 19 maintain a constant flow rate through the sensor.

Calibration of the sensor is performed by exposing it to three gas mixtures (oxygen/nitrogen) of different oxygen concentrations and recording the sensor output for each mixture. A sufficient flow rate of each mixture is supplied to structural tee joint 14 to ensure that no room air enters the sensor. The calibration curve is generated from a least-squares fit of these three data according to the following relation:

$$C = ae^{bv}$$

where:
- $C$ = oxygen concentration in percent
- $a$ = least-squares intercept
- $b$ = least-squares
- $v$ = sensor output in millivolts.

The above relation converts the sensor millivolt output directly to oxygen percent. In this case the sample flow rate was four liters per minute and the sample temperature was 400° F. The calibration gases used were 1%, 10%, and 20% oxygen. In each case, the value calculated from the least-squares determined function is within 0.5% of the true value.

Sensor response time tests were made by switching between two gases of different oxygen concentrations, one being room air and the other being the 10% calibration gas. As in the calibration case, a sufficient flow rate of the 10% gas is maintained to keep out the room air. When the valve closes, room air immediately takes its place. The instant when the 10% gas is switched off is designated by $t_o$. The response time, $t_r$, is defined as the interval between $t_o$ and the instant at which the sensor output reaches 66% of its completed excursion. This is measured on a plotter which is triggered by the same switch that turns off the 10% gas.

As expected, the sample flow rate affects the response time, since increasing flow rate flushes out the sensor volume more quickly. A low flow rate produces a slow response time, and increasing the flow rate beyond a certain level produces no significant improvement in the response time.

The present invention has been described in detail with respect to certain preferred embodiments thereof. As is understood by those of skill in this art, variations and modifications in this detail may be made without any departure from the spirit and scope of the present invention, as defined in the hereto-appended claims.

We claim:

1. A quick response, real-time gaseous measurement system for sampling a low pressure gaseous environment, the system comprising:

pumping means for continuously extracting a sample of test gas from the low pressure gaseous environment and continuously pumping the extracted sample of test gas to a structural tee joint which is open to the atmosphere at one end thereof to ensure a constant pressure downstream thereof;

a heating means for maintaining the test gas at a constant temperature which communicates with the pumping means at the other end thereof;

an oxygen sensor based on a zirconium oxide disc coated with porous platinum, the oxygen sensor communicating with the heating means for developing a voltage which is proportional to the partial pressure of the gaseous component to be measured in the test gas;

calibration means located on the structural tee joint for allowing test gases of various known component concentrations to be sent through the heating means to the sensing means for calibration thereof;

a sample pump cooperating with a flow controller for providing a constant flow rate of test gas through the heating means and sensing means; and means for the introduction of reference air, which is required by the oxygen sensor for optimum operation.

* * * * *